United States Patent [19]
Bandman et al.

[11] Patent Number: 6,008,337
[45] Date of Patent: Dec. 28, 1999

[54] CELL CYCLE RELATED PROTEINS

[75] Inventors: Olga Bandman; Jennifer L. Hillman; Neil C. Corley, all of Mountain View; Karl J. Guegler, Menlo Park; Henry Yue, Sunnyvale; Preeti Lal, Santa Clara, all of Calif.

[73] Assignee: Incyte Pharmaceuticals, Inc., Palo Alto, Calif.

[21] Appl. No.: 09/032,372

[22] Filed: Feb. 27, 1998

[51] Int. Cl.$^6$ .............................. C07H 21/04; C07H 21/02
[52] U.S. Cl. .................... 536/23.5; 536/23.1; 536/24.31; 536/24.3; 530/358; 530/350
[58] Field of Search ................................ 536/23.1, 23.5, 536/24.33, 24.31; 514/44; 424/43.2; 435/325, 252.3, 91.1, 91.4, 69.1; 530/333, 350

[56] References Cited

PUBLICATIONS

Ciechanover, A., "The Ubiquitin–Proteasome Proteolytic Pathway", *Cell*, 79: 13–21 (1994).

Stepanova, L. et al., "Mammalian p50$^{Cdc37}$ is a protein kinase–targeting subunit of Hsp90 that binds and stabilizes Cdk4", *Genes and Development*, 10: 1491–1502 (1996).

Watson, S. And S. Arkinstall, *The G–Protein Linked Receptor FactsBook*, Academic Press, San Diego, CA, pp. 296–314 (1994).

Watson, J.A. et al., "A Novel Form of the G–Protein β Subunit Gβ$_5$ Is Specifically Expressed in the Vertebrate Retina", *J. Biol. Chem.*, 271: 28154–28160 (1996).

Tavitian, A., "Protéines RAS et protéines apparentées", *C.R. Seances Soc. Biol. Fil.*, 189: 7–12 (1995).

Benton, B.K. et al., "Over–expression of *S. Cerevisiae* G$_1$ cyclins restores the viability of a1g1 N–glycosylation mutants", *Curr. Genet.*, 29: 106–113 (1996).

Stepanova, L. et al., (Direct Submission), GenBank Sequence Database (Accession U43077), National Center for Biotechnology Information, National Library of Medicine, Bethesda, Maryland, 20894, (GI 1375484; GI 1375485) (Jul. 24, 1997).

Benton, B.K. et al., (Direct Submission), GenBank Sequence Database (Accession U19608), National Center for Biotechnology Information, National Library of Medicine, Bethesda, Maryland, 20894, (GI 1292897; GI 1292898; GI 639493) (Jun. 30, 1996).

Daniel, J. et al., (Direct Submission), GenBank Sequence Database (Accession Z14134), National Center for Biotechnology Information, National Library of Medicine, Bethesda, Maryland, 20894, (GI 7344; GI 7345) (Mar. 31, 1995).

Daniel J. et al., "Isolation of two novel ras genes in *Dictyostelium discoideum*; evidence for a complex, developmentally regulated ras gene subfamily", *Oncogene*, 9: 501–508 (1994).

Ware, J. and B. Zieger, (Direct Submission), GenBank Sequence Database (Accession U74628), National Center for Biotechnology Information, National Library of Medicine, Bethesda, Maryland, 20894, (GI 1809316; GI 1809317) (Dec. 30, 1997).

Zieger, B. et al., "Alternative Expression of Platelet Glycoprotein Ibβ mRNA from an Adjacent 5' Gene with an Imperfect Polyadenylation Signal Sequence", *J. Clin. Invest.*, 99: 520–525 (1997).

Watson, A.J. et al., (Direct Submission), GenBank Sequence Database (Accession U69145), National Center for Biotechnology Information, National Library of Medicine, Bethesda, Maryland, 20894, (GI 1663628; GI 1663269) (Nov. 8, 1996).

Hillier, L. et al., GenBank Sequence Database (Accession R93646), National Center for Biotechnology Information, National Library of Medicine, Bethesda, Maryland, 20894, Aug. 27, 1995.

Matsubara, K., et al, GenBank Sequence Database (Accession T20314), National Center for Biotechnology Information, National Library of Medicine, Bethesda, Maryland, 20894, Jul. 18, 1996.

Hillier, L., GenBank Sequence Database (Accession N42988), National Center for Biotechnology Information, National Library of Medicine, Bethesda, Maryland, 20894, Jan. 25, 1996.

Strausburg, R., GenBank Sequence Database (Accession AA459232), National Center for Biotechnology Information, National Library of Medicine, Bethesda, Maryland, 20894, Aug. 13, 1997.

Strausburg, R., GenBank Sequence Database (Accession AA557639), National Center for Biotechnology Information, National Library of Medicine, Bethesda, Maryland, 20894, Aug. 14, 1997.

Watson, A.J., et al., "A Fifth Member of the Mammalian g–Protein Beta–Subunit Family," *J. Biol. Chem.*, vol. 269, No. 35, pp. 22150–22156, Sep. 2, 1994.

Grammatikakis, N., et al., "A Novel Glycosaminoglycan––binding Protein Is the Vertebrate Homologue of the Cell Cycle Control Protein, Cdc37," *J. Biol. Chem.* vol. 270, No. 27, pp. 16198–16205, Jul. 7, 1995.

Goethals, K., et al., "An Azorhizobium caulinodans ORS571 Locur Involved in Lipopolysaccharide Production and Nodule Formation on Sesbania rostrata Stems and Roots," *J. Bacteriol.* vol. 176 No. 1, Jan. 1, 1994.

Nottenburg, G., et al., "Lymphocyte HEV adhesion variants differ in the expression of multiple gene sequences," *Gene* 95, pp. 279–284, Aug. 15, 1990.

Tavitian, A., et al., GenBank Sequence Database (Accession R05076), National Center for Biotechnology Information, National Library of Medicine, Bethesda, Maryland, 20894, Jul. 10, 1990.

*Primary Examiner*—Paula K. Hutzell
*Assistant Examiner*—Timothy A. Worrall
*Attorney, Agent, or Firm*—Incyte Pharmaceuticals, Inc; Colette C. Muenzen; Sheela Mohan Peterson

[57] ABSTRACT

The invention provides human cell cycle related proteins (CCRP) and polynucleotides which identify and encode CCRP. The invention also provides expression vectors, host cells, antibodies, agonists, and antagonists. The invention also provides methods for treating or preventing disorders associated with expression of CCRP.

7 Claims, 5 Drawing Sheets

```
204 LEAEKKGALMEQIAHQAVVMQFIMEMAKNC    680517
197 LEVEEKCALMEQVAHQTIVMQFILELAKSL    gi1375485

234 NVDPRGCFRLFFQKAKAEEEGYFEAFKNEL    680517
227 KVDPRACFRQFFTKIKTADRQYMEGFNDEL    gi1375485

264 EAFKSRVR----LYSQSQSFQPMTVQNH      680517
257 EAFKERVRGRAKLRIEKAMKEYEEEERKKR    gi1375485

288 VPHSGVGSIGLLESLPQ-----------      680517
287 LGPGGLDPVEVYESLPEELQKCFDVKDVQM    gi1375485

305 -----NPDY-LQYSISTAL--------       680517
317 LQDAISKMDPTDAKYHMQRCIDSGLWVPNS    gi1375485

318 ------------CSLNSVVHKEDDEPKM      680517
347 KASEAKEGEEAGPGDPLLEAVPKTGDEKDV    gi1375485

334 MDTV                              680517
377 --SV                              gi1375485
```

FIGURE 1B

```
  1 MLKAVILIGGPQKGTRFRPLSFEVPKPLFP           1693222
  1 M-KGLILVGG--YGTRLRPLTVPKPLVE             gl1292898

31 VAGVPMIQHHIEACAQVPGMQEILLIGFYQ           1693222
 28 FGNRPMILHQIEALAN-AGVTDIVLAVNYR           gl1292898

61 PDEPLTQFLEAAQQEFNLPVRYLQEFAPLG           1693222
 57 P-EVMVETLKKYEKEYGVNITFSVETEPLG           gl1292898

91 TGGGLYHFRDQILAGSPEAFFVLNADVCSD           1693222
 86 TAGPL-KLAEDVLKKDNSPFFVLNSDVICE           gl1292898

121 FPLSAMLEAHRRQRHPFLLGTTANRTQSL            1693222
115 YPFKELADFHKAHGGKGTIVATKVD--EPS           gl1292898

151 NYGCIVENPQTHEVL-HYVEKPSTFISDII           1693222
143 KYGVIVHDIATPNLIDRFVEKPKEEFVGNRI          gl1292898

180 NCGIYLFSPEALKPLRDVFQRNQQDGQLED           1693222
173 NAGLYILNPEVI----DLIEMKP-----             gl1292898

210 SPGLWPGAGTIRLEQDVFSALAGQGQIYVH           1693222
192 -------------TSIEKETEPPILVEEKQLYSF       gl1292898
```

FIGURE 2A

```
240 LTDGIWSQIKSAGSALYASRLYLYLSRYQDTH              1693222
212 DLEGFWMDVGQPKDFLSGTVLYLNSLAKRQ                gi1292898

270 PERLAK--HTPGGPMDPRECVHPPDRQGGP                1693222
242 PKKLATGANIVGNALIDPTAKISSTAKIGP                gi1292898

298 LGCAGPQRLHREGGDRGCRVCGSGRASSM                 1693222
272 DVVIGPN-VTIGDGVRITRSVVLCNSTIKN                gi1292898

328 EPLCRSTRVFCIASWAGGAPWDAGRAW-RV                1693222
301 HSLVKST---IVGWNSTVG----QWCRL                  gi1292898

357 PPVTLTPTIPEPAWTVRASSRTGSCCLLSP                1693222
322 EGVTV-------------------------                gi1292898

387 SMGCRVRIPAEVLILNSIVLPHKELSRSFT                1693222
327 -LGDDVEVKDEIYINGGKVLPHKSISDNVP                gi1292898

417 NQ-IIL                                        1693222
356 KEAIIM                                        gi1292898
```

FIGURE 2B

```
1   MWXXAXXL-GAGRVGKSAMIVRFLTKRFIG    2666519
1   MFNFKLVLVGPGGVGKSCLTIQFIAQKFVD    g7345

30  DYEPNTGKLYSRLVYVEGDQLSLQIQDTPG    2666519
31  EYDPTLEDSYRKQTTVDGEECLLDIYDTAG    g7345

60  GVQIQDSLPQVVDSLSKCVQWAEGFLLVYS    2666519
61  ----QEDFSAVRD---QYMRTGEGFLCVYS    g7345

90  ITDYDSYLSIRPLYQHIRKVHPDSKAPVII    2666519
84  ITYLQSFKEIHRLHNHLLKVKDLDSVPFVL    g7345

120 VGNKGDLLHARQVQTQDGIQLANELGSLFL    2666519
114 VGNKCDLNEYREVSTAEGEELAKKLNCKFL    g7345

150 EISTSENYEDVCDVFQHLCKEVSKMHGLSG    2666519
144 ETSAKERI-NVSESFYELVREVKK-----    g7345

180 ERRRASIIPRPRSPNMQDLKRRFKQALSPK    2666519
167 ------ARQSNQHSNSQEQNTDQPI--K    g7345

210 VKAPSALG    2666519
187 KKKSCNLL    g7345
```

FIGURE 3

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 395 amino acids
      (B) TYPE: amino acid
      (C) STRANDEDNESS: single
      (D) TOPOLOGY: linear (vii) IMMEDIATE SOURCE:
      (A) LIBRARY: SYNORAB01
      (B) CLONE: 78191

(xi) SEQUENCE DESCRIPTION: SEQ ID NO:1:

```
Met Xaa Asp Gln Thr Phe Leu Val Asn Val Phe Gly Ser Cys Asp Lys
 1               5                  10                  15

Cys Phe Lys Cys Arg Ser Thr Leu Glu Asp Pro Pro Arg Gly Ser Pro
            20                  25                  30

Leu Pro Ser Pro Leu Arg Pro Arg Ala Lys Met Ala Thr Glu Gly Leu
        35                  40                  45
```

```
His Glu Asn Glu Thr Leu Ala Ser Leu Lys Ser Glu Ala Ser Leu
     50                  55                  60

Lys Gly Lys Leu Glu Glu Arg Ala Lys Leu His Asp Val Glu Leu
 65                  70                  75                  80

His Gln Val Ala Glu Arg Val Glu Ala Leu Gly Gln Phe Val Met Lys
                     85                  90                  95

Thr Arg Arg Thr Leu Lys Gly His Gly Asn Lys Val Leu Cys Met Asp
                100                 105                 110

Trp Cys Lys Asp Lys Arg Ile Val Ser Ser Gln Asp Gly Lys
            115                 120                 125

Val Ile Val Trp Asp Ser Phe Thr Thr Asn Lys Glu His Ala Val Thr
         130                 135                 140

Met Pro Cys Thr Trp Val Met Ala Cys Ala Tyr Ala Pro Ser Gly Cys
145                 150                 155                 160

Ala Ile Ala Cys Gly Gly Leu Asp Asn Lys Cys Ser Val Tyr Pro Leu
                165                 170                 175

Thr Phe Asp Lys Asn Glu Asn Met Ala Ala Lys Lys Ser Val Ala
                180                 185                 190

Met His Thr Asn Tyr Leu Ser Ala Cys Ser Phe Thr Asn Ser Asp Met
        195                 200                 205

Gln Ile Leu Thr Ala Ser Gly Asp Gly Thr Cys Ala Leu Trp Asp Val
        210                 215                 220

Glu Ser Gly Gln Leu Leu Gln Ser Phe His Gly His Gly Ala Asp Val
225                 230                 235                 240

Leu Cys Leu Asp Leu Ala Pro Ser Glu Thr Gly Asn Thr Phe Val Ser
                245                 250                 255

Gly Gly Cys Asp Lys Lys Ala Met Val Trp Asp Met Arg Ser Gly Gln
                260                 265                 270

Cys Val Gln Ala Phe Glu Thr His Glu Ser Asp Ile Asn Ser Val Arg
        275                 280                 285

Tyr Tyr Pro Ser Gly Asp Ala Phe Ala Ser Gly Ser Asp Asp Ala Thr
        290                 295                 300

Cys Arg Leu Tyr Asp Leu Arg Ala Asp Arg Glu Val Ala Ile Tyr Ser
305                 310                 315                 320

Lys Glu Ser Ile Ile Phe Gly Ala Ser Ser Val Asp Phe Ser Leu Ser
                325                 330                 335

Gly Arg Leu Leu Phe Ala Gly Tyr Asn Asp Tyr Thr Ile Asn Val Trp
                340                 345                 350

Asp Val Leu Lys Gly Ser Arg Val Ser Ile Leu Phe Gly His Glu Asn
                355                 360                 365

Arg Val Ser Thr Leu Arg Val Ser Pro Asp Gly Thr Ala Phe Cys Ser
                370                 375                 380

Gly Ser Trp Asp His Thr Leu Arg Val Trp Ala
385                 390                 395

(2) INFORMATION FOR SEQ ID NO:2:

(i) SEQUENCE CHARACTERISTICS:
        (A) LENGTH: 337 amino acids
        (B) TYPE: amino acid
        (C) STRANDEDNESS: single
        (D) TOPOLOGY: linear (vii) IMMEDIATE SOURCE:
        (A) LIBRARY: UTRSNOT02
        (B) CLONE: 680517
```

-continued (xi) SEQUENCE DESCRIPTION: SEQ ID NO:2:

```
Met Glu Gln Pro Trp Pro Pro Gly Pro Trp Ser Leu Pro Arg Ala
 1               5                  10                  15

Glu Gly Glu Ala Glu Glu Ser Asp Phe Asp Val Phe Pro Ser Ser
            20                  25                  30

Pro Arg Cys Pro Gln Leu Pro Gly Gly Ala Gln Met Tyr Ser His
            35                  40                  45

Gly Ile Glu Leu Ala Cys Gln Lys Gln Lys Glu Phe Val Lys Ser Ser
 50                  55                  60

Val Ala Cys Lys Trp Asn Leu Ala Glu Ala Gln Gln Lys Leu Gly Ser
 65                  70                  75                  80

Leu Ala Leu His Asn Ser Glu Ser Leu Asp Gln Glu His Ala Lys Ala
                     85                  90                  95

Gln Thr Ala Val Ser Glu Leu Arg Gln Arg Glu Glu Trp Arg Gln
            100                 105                 110

Lys Glu Glu Ala Leu Val Gln Arg Glu Lys Met Cys Leu Trp Ser Thr
            115                 120                 125

Asp Ala Ile Ser Lys Asp Val Phe Asn Lys Ser Phe Ile Asn Gln Asp
130                 135                 140

Lys Arg Lys Asp Thr Glu Asp Glu Asp Lys Ser Glu Ser Phe Met Gln
145                 150                 155                 160

Lys Tyr Glu Gln Lys Ile Arg His Phe Gly Met Leu Ser Arg Trp Asp
                165                 170                 175

Asp Ser Gln Arg Phe Leu Ser Asp His Pro Tyr Leu Val Cys Glu Glu
            180                 185                 190

Thr Ala Lys Tyr Leu Ile Leu Trp Cys Phe His Leu Glu Ala Glu Lys
            195                 200                 205

Lys Gly Ala Leu Met Glu Gln Ile Ala His Gln Ala Val Val Met Gln
210                 215                 220

Phe Ile Met Glu Met Ala Lys Asn Cys Asn Val Asp Pro Arg Gly Cys
225                 230                 235                 240

Phe Arg Leu Phe Phe Gln Lys Ala Lys Ala Glu Glu Glu Gly Tyr Phe
                245                 250                 255

Glu Ala Phe Lys Asn Glu Leu Glu Ala Phe Lys Ser Arg Val Arg Leu
            260                 265                 270

Tyr Ser Gln Ser Gln Ser Phe Gln Pro Met Thr Val Gln Asn His Val
            275                 280                 285

Pro His Ser Gly Val Gly Ser Ile Gly Leu Leu Glu Ser Leu Pro Gln
290                 295                 300

Asn Pro Asp Tyr Leu Gln Tyr Ser Ile Ser Thr Ala Leu Cys Ser Leu
305                 310                 315                 320

Asn Ser Val Val His Lys Glu Asp Glu Pro Lys Met Met Asp Thr
                325                 330                 335

Val
```

(2) INFORMATION FOR SEQ ID NO:3:

(i) SEQUENCE CHARACTERISTICS:
        (A) LENGTH: 421 amino acids
        (B) TYPE: amino acid
        (C) STRANDEDNESS: single
        (D) TOPOLOGY: linear (vii) IMMEDIATE SOURCE:
        (A) LIBRARY: COLNNOT23
        (B) CLONE: 1693222

(xi) SEQUENCE DESCRIPTION: SEQ ID NO:3:

```
Met Leu Lys Ala Val Ile Leu Ile Gly Gly Pro Gln Lys Gly Thr Arg
 1               5                  10                  15

Phe Arg Pro Leu Ser Phe Glu Val Pro Lys Pro Leu Phe Pro Val Ala
            20                  25                  30

Gly Val Pro Met Ile Gln His His Ile Glu Ala Cys Ala Gln Val Pro
                35                  40                  45

Gly Met Gln Glu Ile Leu Leu Ile Gly Phe Tyr Gln Pro Asp Glu Pro
     50                  55                  60

Leu Thr Gln Phe Leu Glu Ala Ala Gln Gln Phe Asn Leu Pro Val
 65                  70                  75                  80

Arg Tyr Leu Gln Glu Phe Ala Pro Leu Gly Thr Gly Gly Leu Tyr
                85                  90                  95

His Phe Arg Asp Gln Ile Leu Ala Gly Ser Pro Glu Ala Phe Phe Val
                100                 105                 110

Leu Asn Ala Asp Val Cys Ser Asp Phe Pro Leu Ser Ala Met Leu Glu
            115                 120                 125

Ala His Arg Arg Gln Arg His Pro Phe Leu Leu Leu Gly Thr Thr Ala
        130                 135                 140

Asn Arg Thr Gln Ser Leu Asn Tyr Gly Cys Ile Val Glu Asn Pro Gln
145                 150                 155                 160

Thr His Glu Val Leu His Tyr Val Glu Lys Pro Ser Thr Phe Ile Ser
                165                 170                 175

Asp Ile Ile Asn Cys Gly Ile Tyr Leu Phe Ser Pro Glu Ala Leu Lys
                180                 185                 190

Pro Leu Arg Asp Val Phe Gln Arg Asn Gln Gln Asp Gly Gln Leu Glu
            195                 200                 205

Asp Ser Pro Gly Leu Trp Pro Gly Ala Gly Thr Ile Arg Leu Glu Gln
        210                 215                 220

Asp Val Phe Ser Ala Leu Ala Gly Gln Gly Gln Ile Tyr Val His Leu
225                 230                 235                 240

Thr Asp Gly Ile Trp Ser Gln Ile Lys Ser Ala Gly Ser Ala Leu Tyr
                245                 250                 255

Ala Ser Arg Leu Tyr Leu Ser Arg Tyr Gln Asp Thr His Pro Glu Arg
                260                 265                 270

Leu Ala Lys His Thr Pro Gly Gly Pro Met Asp Pro Arg Glu Cys Val
            275                 280                 285

His Pro Pro Asp Arg Gln Gly Gly Pro Leu Gly Cys Ala Gly Pro Gln
        290                 295                 300

Arg Leu His Arg Glu Gly Gly Asp Arg Gly Cys Arg Val Cys Gly Ser
305                 310                 315                 320

Gly Arg Ala Ser Ser Ser Met Glu Pro Leu Cys Arg Ser Thr Arg Val
                325                 330                 335

Phe Cys Ile Ala Ser Trp Ala Gly Gly Ala Pro Trp Asp Ala Gly Arg
                340                 345                 350

Ala Trp Arg Val Pro Pro Val Thr Leu Thr Pro Thr Ile Pro Glu Pro
            355                 360                 365

Ala Trp Thr Val Arg Ala Ser Ser Arg Thr Gly Ser Cys Cys Leu Leu
        370                 375                 380

Ser Pro Ser Met Gly Cys Arg Val Arg Ile Pro Ala Glu Val Leu Ile
385                 390                 395                 400

Leu Asn Ser Ile Val Leu Pro His Lys Glu Leu Ser Arg Ser Phe Thr
                405                 410                 415
```

Asn Gln Ile Ile Leu
420

(2) INFORMATION FOR SEQ ID NO:4:

(i) SEQUENCE CHARACTERISTICS:
        (A) LENGTH: 367 amino acids
        (B) TYPE: amino acid
        (C) STRANDEDNESS: single
        (D) TOPOLOGY: linear (vii) IMMEDIATE SOURCE:
        (A) LIBRARY: BRAITUT21
        (B) CLONE: 2522306

(xi) SEQUENCE DESCRIPTION: SEQ ID NO:4:

Met Asp Lys Glu Tyr Val Gly Phe Ala Ala Leu Pro Asn Gln Leu His
1               5                   10                  15

Arg Lys Ser Val Lys Lys Gly Phe Asp Phe Thr Leu Met Val Ala Gly
            20                  25                  30

Glu Ser Gly Leu Gly Lys Ser Thr Leu Ile Asn Ser Leu Phe Leu Thr
        35                  40                  45

Asn Leu Tyr Glu Asp Arg Gln Val Pro Glu Ala Ser Ala Arg Leu Thr
    50                  55                  60

Gln Thr Leu Ala Ile Glu Arg Gly Val Glu Ile Glu Glu Gly Gly
65                  70                  75                  80

Val Lys Val Lys Leu Thr Leu Val Asp Thr Pro Gly Phe Gly Asp Ser
                85                  90                  95

Val Asp Cys Ser Asp Cys Trp Leu Pro Val Lys Phe Ile Glu Glu
                100                 105                 110

Gln Phe Glu Gln Tyr Leu Arg Asp Glu Ser Gly Leu Asn Arg Lys Asn
            115                 120                 125

Ile Gln Asp Ser Arg Val His Cys Cys Leu Tyr Phe Ile Ser Pro Phe
        130                 135                 140

Gly Arg Gly Leu Arg Pro Leu Asp Val Ala Phe Leu Arg Ala Val His
145                 150                 155                 160

Glu Lys Val Asn Ile Ile Pro Val Ile Gly Lys Ala Asp Ala Leu Met
                165                 170                 175

Pro Gln Glu Thr Gln Ala Leu Lys Gln Lys Ile Arg Asp Gln Leu Lys
            180                 185                 190

Glu Glu Glu Ile His Ile Tyr Gln Phe Pro Glu Cys Asp Ser Asp Glu
        195                 200                 205

Asp Glu Asp Phe Lys Arg Gln Asp Ala Glu Met Lys Glu Ser Ile Pro
    210                 215                 220

Phe Ala Val Val Gly Ser Cys Glu Val Val Arg Asp Gly Gly Asn Arg
225                 230                 235                 240

Pro Val Arg Gly Arg Arg Tyr Ser Trp Gly Thr Val Glu Val Glu Asn
                245                 250                 255

Pro His His Cys Asp Phe Leu Asn Leu Arg Arg Met Leu Val Gln Thr
            260                 265                 270

His Leu Gln Asp Leu Lys Glu Val Thr His Asp Leu Leu Tyr Glu Gly
        275                 280                 285

Tyr Arg Ala Arg Cys Leu Gln Ser Leu Ala Arg Pro Gly Ala Arg Asp
    290                 295                 300

Arg Ala Ser Arg Ser Lys Leu Ser Arg Gln Ser Ala Thr Glu Ile Pro
305                 310                 315                 320

Leu Pro Met Leu Pro Leu Ala Asp Thr Glu Lys Leu Ile Arg Glu Lys
                325                 330                 335

```
Asp Glu Glu Leu Arg Arg Met Gln Met Leu Glu Lys Met Gln Ala
            340                 345                 350
Gln Met Gln Gln Ser Gln Ala Gln Gly Glu Gln Ser Asp Ala Leu
        355                 360                 365

(2) INFORMATION FOR SEQ ID NO:5:

(i) SEQUENCE CHARACTERISTICS:
        (A) LENGTH: 217 amino acids
        (B) TYPE: amino acid
        (C) STRANDEDNESS: single
        (D) TOPOLOGY: linear (vii) IMMEDIATE SOURCE:
        (A) LIBRARY: PENCNOT01
        (B) CLONE: 2666519

(xi) SEQUENCE DESCRIPTION: SEQ ID NO:5:

Met Trp Xaa Xaa Ala Xaa Xaa Leu Gly Ala Gly Arg Val Gly Lys Ser
 1               5                  10                  15
Ala Met Ile Val Arg Phe Leu Thr Lys Arg Phe Ile Gly Asp Tyr Glu
            20                  25                  30
Pro Asn Thr Gly Lys Leu Tyr Ser Arg Leu Val Tyr Val Glu Gly Asp
        35                  40                  45
Gln Leu Ser Leu Gln Ile Gln Asp Thr Pro Gly Gly Val Gln Ile Gln
    50                  55                  60
Asp Ser Leu Pro Gln Val Val Asp Ser Leu Ser Lys Cys Val Gln Trp
65                  70                  75                  80
Ala Glu Gly Phe Leu Leu Val Tyr Ser Ile Thr Asp Tyr Asp Ser Tyr
                85                  90                  95
Leu Ser Ile Arg Pro Leu Tyr Gln His Ile Arg Lys Val His Pro Asp
            100                 105                 110
Ser Lys Ala Pro Val Ile Ile Val Gly Asn Lys Gly Asp Leu Leu His
        115                 120                 125
Ala Arg Gln Val Gln Thr Gln Asp Gly Ile Gln Leu Ala Asn Glu Leu
    130                 135                 140
Gly Ser Leu Phe Leu Glu Ile Ser Thr Ser Glu Asn Tyr Glu Asp Val
145                 150                 155                 160
Cys Asp Val Phe Gln His Leu Cys Lys Glu Val Ser Lys Met His Gly
                165                 170                 175
Leu Ser Gly Glu Arg Arg Arg Ala Ser Ile Ile Pro Arg Pro Arg Ser
            180                 185                 190
Pro Asn Met Gln Asp Leu Lys Arg Arg Phe Lys Gln Ala Leu Ser Pro
        195                 200                 205
Lys Val Lys Ala Pro Ser Ala Leu Gly
    210                 215

(2) INFORMATION FOR SEQ ID NO:6:

(i) SEQUENCE CHARACTERISTICS:
        (A) LENGTH: 2119 base pairs
        (B) TYPE: nucleic acid
        (C) STRANDEDNESS: single
        (D) TOPOLOGY: linear (vii) IMMEDIATE SOURCE:
        (A) LIBRARY: SYNORAB01
        (B) CLONE: 78191

(xi) SEQUENCE DESCRIPTION: SEQ ID NO:6:

CTCACCTCTC ACCATCTGCT CTGTGGCTCC CAGTGCTGAC TCTGGAAGCT TTATCTTGGG      60
```

```
TAAAAGATGT NTGATCAGAC CTTTCTCGTT AATGTATTTG GCTCATGTGA CAAATGTTTC      120

AAATGCAGGT CGACTCTAGA GGATCCCCCT CGAGGCTCTC CGCTTCCCTC TCCGCTGCGT      180

CCCCGCGCGA AGATGGCAAC CGAGGGGCTG CACGAGAACG AGACGCTGGC GTCGCTGAAG     240

AGCGAGGCCG AGAGCCTCAA GGGCAAGCTG GAGGAGGAGC GAGCCAAGCT GCACGATGTG      300

GAGCTGCACC AGGTGGCGGA GCGGGTGGAG GCCCTGGGGC AGTTTGTCAT GAAGACCAGA      360

AGGACCCTCA AAGGCCACGG GAACAAAGTC CTGTGCATGG ACTGGTGCAA AGATAAGAGG      420

AGGATCGTGA GCTCGTCACA GGATGGGAAG GTGATCGTGT GGGATTCCTT CACCACAAAC      480

AAGGAGCACG CGGTCACCAT GCCCTGCACG TGGGTGATGG CATGTGCTTA TGCCCCATCG      540

GGATGTGCCA TTGCTTGTGG TGGTTTGGAT AATAAGTGTT CTGTGTACCC CTTGACGTTT      600

GACAAAAATG AAAACATGGC TGCCAAAAAG AAGTCTGTTG CTATGCACAC CAACTACCTG      660

TCGGCCTGCA GCTTCACCAA CTCTGACATG CAGATCCTGA CAGCGAGCGG CGATGGCACA      720

TGTGCCCTGT GGGACGTGGA GAGCGGGCAG CTGCTGCAGA GCTTCCACGG ACATGGGGCT      780

GACGTCCTCT GCTTGGACCT GGCCCCCTCA GAAACTGGAA ACACCTTCGT GTCTGGGGGA      840

TGTGACAAGA AAGCCATGGT GTGGGACATG CGCTCCGGCC AGTGCGTGCA GGCCTTTGAA      900

ACACATGAAT CTGACATCAA CAGTGTCCGG TACTACCCCA GTGGAGATGC CTTTGCTTCA      960

GGGTCAGATG ACGCTACGTG TCGCCTCTAT GACCTGCGGG CAGATAGGGA GGTTGCCATC      1020

TATTCCAAAG AAAGCATCAT ATTTGGAGCA TCCAGCGTGG ACTTCTCCCT CAGTGGTCGC      1080

CTGCTGTTTG CTGGATACAA TGATTACACT ATCAACGTCT GGGATGTTCT CAAAGGGTCC      1140

CGGGTCTCCA TCCTGTTTGG ACATGAAAAC CGCGTTAGCA CTCTACGAGT TTCCCCCGAT      1200

GGGACTGCTT TCTGCTCTGG ATCATGGGAT CATACCCTCA GAGTCTGGGC CTAATCATCT      1260

TCTGACAGTG CACTCATGTA TACCTGAGAA TTTGAAATCT TCACATGTAA ATAGATATTA      1320

CTTCTAGAGG AGCTTAGAGT TTATTGCAGT GTAGCTTAGG GGAGCAACCC ATGGCTCACA      1380

GGTCACTAAG CGTCTCCAAT ATGACTATTA AAACTGTCAC CTCTGGAAAT ACACTAGTGT      1440

GAGCCTTCAG CACTGCGAGA ATACCTTCAA GTACAGTATT TTTCTTTTGG AACACTTTTT      1500

AAAATGTATC TGTTTTTAAG GTTATTCTAA ATTATAGTAG CCTCAACTCA TTCTGTCACC      1560

AGTAGAATTC AGCAGTTAAT ATATTCCATA TTATTTCTTT GAATCAATTC ATTTTCAGAG      1620

CACTTTAAAG TCTGATATTT CTCGATGTGC ACTGTGATGC CTGGAACCTT CCTCTGGAAG      1680

TGCTGATTTT ATGGACTGAG GACTGGTGAC TGGTCTGTGA TAGAAGCAAA TTCCAATTCC      1740

AAATGTAATT AGACAAAAAT CATTTTTTTA GAATGTGTTT TTATTGTAAA AGTATCTTTT      1800

TCAGCTTCCT GTTCTATTGT CTTTTTTCAG ATACAACATT TTTGTCTATG GTGAACTGCT      1860

GTAAATGACG CAGAGAAATG CCTAAAAAGG ACAGGTGGTT TGACTCATGG ATGATGATGA      1920

TGTCACTGTG CCACTTGGAC AGGGCGTTTT CTCTGAATTG AAGGGAAAGC CAATGGTGTT      1980

TGTAAACAAA TGCTTCTGAG AGCAAAGAAA AGTCTTCTGT GTGGGAACAC AAGATAGTAA      2040

ACTTATTTAA AAACCTATTA GTAGAATTAG TGGAAACACT TAGGTTAAAG TGAATCTTGT      2100

CCATATAAAT NATATTCAT                                                   2119

(2) INFORMATION FOR SEQ ID NO:7:

(i) SEQUENCE CHARACTERISTICS:
        (A) LENGTH: 1600 base pairs
        (B) TYPE: nucleic acid
        (C) STRANDEDNESS: single
        (D) TOPOLOGY: linear
```

```
            (vii) IMMEDIATE SOURCE:
                  (A) LIBRARY: URSNOT02
                  (B) CLONE: 680517

(xi) SEQUENCE DESCRIPTION: SEQ ID NO:7:

GCTGTCGCCG GGTGTGCAGC GGCGTCGCGG CCAGTAGAGG GATTCTGGGT AACGGCCCGG      60

ACCCCCGGCT GGGCTTCTGG CTCGGCGCAC AGGTTCCATT CACGCCAAGT CTGTTGGCAG     120

TGGCAGTTGT AGGGCCAAGG GCGGTTGTAG GACCCGGAGC AGCCGGACAT GGAACAACCG     180

TGGCCGCCTC CGGGACCCTG GAGCCTCCCT CGGGCCGAGG GTGAGGCTGA GGAAGAGAGT     240

GACTTCGACG TGTTCCCCAG TTCTCCCCGC TGCCCGCAGC TGCCAGGCGG CGGCGCCCAG     300

ATGTATAGCC ATGGAATTGA ATTGGCTTGC CAAAAGCAGA AAGAGTTTGT GAAGAGCTCT     360

GTGGCGTGCA AATGGAATCT TGCTGAAGCT CAACAGAAAC TTGGTAGCTT AGCACTGCAT     420

AATTCTGAGT CTTTGGATCA GGAGCATGCC AAAGCACAAA CAGCAGTATC AGAACTGAGG     480

CAACGGGAAG AAGAGTGGCG ACAGAAAGAA GAAGCTCTAG TACAAAGAGA GAAGATGTGT     540

CTGTGGAGCA CGGATGCCAT TAGCAAGGAT GTTTTTAATA AGAGTTTTAT TAATCAAGAT     600

AAAAGAAAAG ACACAGAAGA TGAAGATAAA TCAGAATCAT TTATGCAAAA ATATGAGCAA     660

AAAATCAGAC ATTTTGGTAT GTTGAGTCGA TGGGATGATA GCCAGAGATT TTTGTCTGAC     720

CATCCATACC TTGTATGTGA AGAAACTGCT AAATATCTTA TTTTATGGTG TTTTCACCTG     780

GAAGCTGAGA AGAAAGGGGC TTTAATGGAA CAAATAGCAC ATCAAGCTGT TGTAATGCAG     840

TTTATTATGG AAATGGCCAA AAACTGTAAT GTGGATCCAA GAGGGTGTTT TCGTTTATTT     900

TTTCAGAAAG CGAAAGCAGA GGAAGAAGGT TATTTTGAAG CATTCAAAAA TGAACTTGAA     960

GCTTTCAAGT CAAGAGTAAG ACTTTATTCT CAATCACAAA GTTTTCAACC TATGACAGTT    1020

CAGAATCATG TTCCCCATTC TGGTGTTGGA TCTATAGGTT TATTAGAATC CTTACCACAG    1080

AATCCAGATT ATCTTCAGTA TTCTATCAGT ACAGCTCTCT GCAGCTTAAA CTCGGTGGTA    1140

CATAAAGAAG ATGATGAACC CAAAATGATG GACACTGTAT AATTTGGTTA AGACTGCTGA    1200

GGCCAAGTGC TATTTTGTTA CAAGAAAGGA AGAACTTGGC TATTTTCTTG ACACTTTTAT    1260

GGGTGCTGCA CTTTATTTTT GTTCGGTTTT TGATGGGAGG GAAAGAGTAC TGAAATGTTT    1320

TGTAAATTTT TTTTAATGTG CTGCTAGGTT TTTTGTTTTG TTTTGTTCTG AAGAGAAGAG    1380

TGGTACCATA TGTTGCAGGA AGTCAAACTG GACTTTTTGT GGCTACTAAA TTTGCTTTTA    1440

ATCTTATTGT TCTCAATTTT GGAATCAAGT ATGAAAATCT GCACAAATGC AATGTTTACA    1500

AGAACTGGTT GATTCTGGGA GGCATCTGCT ACAGTCTCTT TTTATATGGA TATGTACATG    1560

TCCTATTCTA CAAAAATGAT TAAAGATAAA AACATACTTG                          1600

(2) INFORMATION FOR SEQ ID NO:8:

(i) SEQUENCE CHARACTERISTICS:
            (A) LENGTH: 1535 base pairs
            (B) TYPE: nucleic acid
            (C) STRANDEDNESS: single
            (D) TOPOLOGY: linear (vii) IMMEDIATE SOURCE:
            (A) LIBRARY: COLNNOT23
            (B) CLONE: 1693222

(xi) SEQUENCE DESCRIPTION: SEQ ID NO:8:

GCGGAAGGAG CTTGCAGTAG CGGGCGGCAG AGCTGGAGTG AAGGGAGCTA GTGTTTAGGT      60

AGCAGTCACC ATTATGCTCA AAGCGGTGAT CCTGATTGGA GGCCCTCAAA AGGGAACTCG     120

CTTCAGACCT TGTCTTTTG AGGTGCCCAA ACCATTGTTT CCTGTGGCAG GGGTCCCTAT     180
```

```
GATCCAACAC CATATTGAAG CCTGTGCCCA GGTCCCTGGA ATGCAGGAGA TTCTGCTCAT    240

TGGCTTCTAC CAACCTGATG AGCCCCTCAC CCAGTTCCTA GAAGCCGCCC AGCAGGAGTT    300

TAACCTTCCA GTCAGGTACC TGCAGGAATT TGCCCCCCTA GGCACAGGGG GTGGTCTTTA    360

CCATTTTCGA GACCAGATCC TGGCTGGGAG CCCCGAGGCA TTCTTCGTGC TCAATGCTGA    420

TGTCTGCTCC GACTTCCCCT TGAGTGCTAT GTTGGAAGCC CACCGACGCC AGCGTCACCC    480

TTTCTTACTC CTTGGCACTA CGGCTAACAG GACGCAATCC CTCAACTACG GCTGCATCGT    540

TGAGAATCCA CAGACACACG AGGTATTGCA CTATGTGGAG AAACCCAGCA CATTTATCAG    600

TGACATCATC AACTGCGGCA TCTACCTCTT TTCTCCTGAA GCCTTGAAGC TCTTCGGGA    660

TGTCTTCCAG CGTAATCAGC AGGATGGGCA ATTGGAGGAC TCACCAGGCT TGTGGCCAGG    720

GGCAGGTACC ATCCGCCTAG AGCAGGATGT GTTTTCAGCC CTGGCAGGGC AGGGCCAGAT    780

ATACGTGCAT CTCACTGATG GTATCTGGAG TCAGATCAAG TCCGCAGGTT CAGCCCTCTA    840

CGCCTCCCGC CTCTACCTGA GCCGATACCA GGACACTCAC CCAGAACGGC TGGCCAAGCA    900

CACCCCAGGG GGGCCCATGG ATCCGAGGGA ATGTGTACAT CCACCCGACC GCCAAGGTGG    960

CCCCCTCGGC TGTGCTGGGC CCCAACGTCT CCATCGGGAA GGGGGTGACC GTGGGTGTAG   1020

GGTGTGCGGC TCCGGGAGAG CATCGTCCTC CATGGAGCCA CTTTGCAGGA GCACACGTGT   1080

GTTCTGCATA GCATCGTGGG CTGGGGGAGC ACCGTGGGAC GCTGGGCGCG CGTGGAGGGT   1140

ACCCCCAGTG ACCCTAACCC CAACGATCCC CGAGCCCGCA TGGACAGTGA GAGCCTCTTC   1200

AAGGACGGGA AGCTGCTGCC TGCTATCACC ATCCATGGGC TGCCGAGTCC GGATCCCTGC   1260

CGAGGTGCTC ATCCTGAACT CGATTGTTCT GCCACACAAG GAGCTGAGCC GAAGCTTCAC   1320

CAACCAGATC ATCCTCTGAG TAGGGCTGCC AGAAGGCCCC CAGCTCCTAC CCACTCCCCT   1380

TGAGGCTGCT GCCTGCTTGG CCAGCCTCTG TCCAGAAAGG ACCAGAGAAA GCCAGGCTGG   1440

ATCGTCACAT GCCGGGAGC AATGTGGATG GCCTGGGAC TCCTGGGTTT CTCCCTCCC   1500

GACTCCCTAA TAAACCCCGT GAACCTTAAA AAAAA                              1535

(2) INFORMATION FOR SEQ ID NO:9:

(i) SEQUENCE CHARACTERISTICS:
        (A) LENGTH: 1341 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2522306

(xi) SEQUENCE DESCRIPTION: SEQ ID NO:9:

CGGGAGAGAC GGCAGGTGCA GTGATGGCTG GCGGAGTCAT GGACAAGGAG TACGTGGGTT     60

TTGCTGCTCT CCCCAACCAG CTGCACCGCA AGTCTGTCAA GAAGGGGTTT GACTTCACGC    120

TAATGGTGGC AGGGGAGTCA GGCCTAGGGA AATCCACCCT CATCAACAGC CTCTTCCTCA    180

CCAACCTCTA TGAGGATCGC CAGGTGCCAG AGGCCAGTGC TCGCTTGACA CAGACCCTGG    240

CCATTGAGCG CCGGGGCGTA GAGATTGAGG AAGGGGGTGT GAAAGTGAAG CTGACCCTTG    300

TGGACACACC TGGCTTTGGG GACTCAGTGG ACTGCTCTGA CTGCTGGCTT CCGGTGGTGA    360

AATTCATCGA GGAGCAATTT GAGCAGTACC TTAGGGATGA GAGTGGCCTG AACCGGAAGA    420

ACATCCAGGA CTCCCGAGTC CACTGCTGCC TCTACTTCAT CTCACCCTTC GGCCGGGGGC    480

TCCGGCCCCT AGATGTGGCC TTCCTCCGGG CAGTACACGA GAAAGTCAAC ATCATCCCAG    540
```

-continued

```
TCATTGGCAA AGCGGATGCT CTGATGCCCC AGGAAACCCA GGCCCTCAAG CAGAAGATCC      600

GGGATCAGTT GAAGGAAGAG GAGATCCACA TCTACCAGTT CCCCGAATGT GACTCTGATG      660

AAGATGAAGA CTTCAAGAGG CAGGATGCAG AGATGAAGGA AAGCATCCCT TTTGCAGTCG      720

TGGGATCATG CGAGGTGGTG AGGGATGGCG GGAACCGGCC GGTGAGGGGA CGCCGCTACT      780

CCTGGGGGAC CGTGGAGGTG GAGAACCCAC ATCACTGCGA TTTCCTGAAC CTGCGACGGA      840

TGCTGGTGCA GACACACCTG CAGGACCTGA AAGAGGTGAC GCACGATCTG CTCTACGAGG      900

GCTACCGGGC CCGCTGCCTA CAGAGCCTGG CCCGGCCTGG GGCTCGCGAT CGAGCCAGCC      960

GCAGTAAGCT TTCCCGCCAG AGCGCCACAG AGATCCCGCT GCCCATGCTG CCTCTGGCGG     1020

ACACCGAGAA GCTGATCCGC GAGAAAGACG AAGAGCTGCG CCGCATGCAA GAGATGCTGG     1080

AGAAGATGCA GGCCCAAATG CAGCAGAGCC AGGCCCAGGG CGAGCAGTCA GACGCCCTCT     1140

GAGGCCACGC CCCGCCCGGC CTTANCTCGG CTCCGCCTTC AGTCGGCCTC TTGTCCAATC     1200

CCCGCGCCCC ACAACTGCCC AGCNCCCCCC GGGACCTCCG GCNGGTGCCG CCCTCGCGCG     1260

GGCTAGGGGG AGGTCTCCCA GCCTGAGTCC GTAGCCCCGC CCCGGCNCTG GTCCCGCNCA     1320

CCCAGACACC GCCCATTCNC G                                               1341
```

(2) INFORMATION FOR SEQ ID NO:10:

(i) SEQUENCE CHARACTERISTICS:
        (A) LENGTH: 960 base pairs
        (B) TYPE: nucleic acid
        (C) STRANDEDNESS: single
        (D) TOPOLOGY: linear (vii) IMMEDIATE SOURCE:
        (A) LIBRARY: PENCNOT01
        (B) CLONE: 2666519

(xi) SEQUENCE DESCRIPTION: SEQ ID NO:10:

```
GGTTTNCCCC NACNTGGGAA AANCGGGCCA ATTGAGCCGC AACGCAATTA AATGTGGNTT       60

TNGGCTNACN CATTGGGCGC CGGCCGCGTG GGCAAGAGCG CAATGATCGT GCGCTTCCTG      120

ACCAAGAGAT TCATTGGAGA CTATGAACCG AATACAGGCA AGCTGTATTC ACGGCTGGTC      180

TATGTCGAGG GGGACCAGCT CTCCCTGCAG ATCCAGGATA CTCCCGGGGG CGTCCAGATC      240

CAAGACAGCC TCCCCCAGGT CGTCGATTCC CTGTCCAAAT GCGTGCAGTG GGCCGAGGGT      300

TTTCTGCTGG TCTATTCCAT CACAGACTAT GACAGCTACT TGTCCATCCG ACCCCTTTAT      360

CAGCACATCC GGAAGGTCCA CCCTGACTCT AAAGCCCCTG TCATCATCGT GGGCAACAAG      420

GGGGACCTTT TGCATGCCCG GCAGGTGCAG ACACAGGACG GTATTCAGCT AGCCAATGAG      480

CTGGGCAGCC TGTTCCTTGA AATTTCCACT AGCGAAAACT ACGAAGATGT CTGTGATGTG      540

TTTCAGCATC TCTGCAAAGA AGTGAGCAAG ATGCACGGCC TCAGTGGGGA AAGAAGAAGA      600

GCCTCCATCA TCCCTCGGCC CCGCTCTCCC AACATGCAGG ACCTGAAGAG ACGCTTCAAG      660

CAGGCTCTGT CTCCCAAAGT CAAAGCCCCC TCTGCACTGG GGTGAACTAT CTCAGACAGA      720

TGCCTCTCCT TTTTAATACG CATTTGTGCA GCTAAAAGAC TGGGCTTCTC GCTTTTTAAT      780

CACACATTCA GAGTTTATTT TTATAAAANA ATTGATTTTC AAGTACATGT GTATTTCTGA      840

AAATTCCAAC CGTGATTGCC TAGAAGCTGG GATAAAATTT GTTTTGTTTT AATAAAAGAA      900

ACTTTTTTTT TNNNNNNNTT TNNTTTTTNN ANAGGNAACN GGGGGGCCCN TTTCCCNAAA      960
```

(2) INFORMATION FOR SEQ ID NO:11:

(i) SEQUENCE CHARACTERISTICS:
        (A) LENGTH: 378 amino acids

```
            (B) TYPE: amino acid
            (C) STRANDEDNESS: single
            (D) TOPOLOGY: linear (vii) IMMEDIATE SOURCE:
            (A) LIBRARY: GenBank
            (B) CLONE: 1375485

(xi) SEQUENCE DESCRIPTION: SEQ ID NO:11:

Met Val Asp Tyr Ser Val Trp Asp His Ile Glu Val Ser Asp Asp Glu
 1               5                  10                  15

Asp Glu Thr His Pro Asn Ile Asp Thr Ala Ser Leu Phe Arg Trp Arg
             20                  25                  30

His Gln Ala Arg Val Glu Arg Met Glu Gln Phe Gln Lys Glu Lys Glu
         35                  40                  45

Glu Leu Asp Arg Gly Cys Arg Glu Cys Lys Arg Lys Val Ala Glu Cys
     50                  55                  60

Gln Arg Lys Leu Lys Glu Leu Glu Val Ala Glu Gly Lys Ala Glu
65                  70                  75                  80

Leu Glu Arg Leu Gln Ala Glu Ala Gln Gln Leu Arg Lys Glu Arg
             85                  90                  95

Ser Trp Glu Gln Lys Leu Glu Glu Met Arg Lys Lys Glu Lys Ser Met
            100                 105                 110

Pro Trp Asn Val Asp Thr Leu Ser Lys Asp Gly Phe Ser Lys Ser Met
            115                 120                 125

Val Asn Thr Lys Pro Glu Lys Thr Glu Glu Asp Ser Glu Glu Val Arg
    130                 135                 140

Glu Gln Lys His Lys Thr Phe Val Glu Lys Tyr Glu Lys Gln Ile Lys
145                 150                 155                 160

His Phe Gly Met Leu Arg Arg Trp Asp Asp Ser Gln Lys Tyr Leu Ser
                165                 170                 175

Asp Asn Val His Leu Val Cys Glu Glu Thr Ala Asn Tyr Leu Val Ile
            180                 185                 190

Trp Cys Ile Asp Leu Glu Val Glu Glu Lys Cys Ala Leu Met Glu Gln
            195                 200                 205

Val Ala His Gln Thr Ile Val Met Gln Phe Ile Leu Glu Leu Ala Lys
    210                 215                 220

Ser Leu Lys Val Asp Pro Arg Ala Cys Phe Arg Gln Phe Phe Thr Lys
225                 230                 235                 240

Ile Lys Thr Ala Asp Arg Gln Tyr Met Glu Gly Phe Asn Asp Glu Leu
                245                 250                 255

Glu Ala Phe Lys Glu Arg Val Arg Gly Arg Ala Lys Leu Arg Ile Glu
            260                 265                 270

Lys Ala Met Lys Glu Tyr Glu Glu Glu Arg Lys Lys Arg Leu Gly
    275                 280                 285

Pro Gly Gly Leu Asp Pro Val Glu Val Tyr Glu Ser Leu Pro Glu Glu
    290                 295                 300

Leu Gln Lys Cys Phe Asp Val Lys Asp Val Gln Met Leu Gln Asp Ala
305                 310                 315                 320

Ile Ser Lys Met Asp Pro Thr Asp Ala Lys Tyr His Met Gln Arg Cys
                325                 330                 335

Ile Asp Ser Gly Leu Trp Val Pro Asn Ser Lys Ala Ser Glu Ala Lys
            340                 345                 350

Glu Gly Glu Glu Ala Gly Pro Gly Asp Pro Leu Leu Glu Ala Val Pro
    355                 360                 365

Lys Thr Gly Asp Glu Lys Asp Val Ser Val
```

370                375

(2) INFORMATION FOR SEQ ID NO:12:

(i) SEQUENCE CHARACTERISTICS:
        (A) LENGTH: 361 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1292898

(xi) SEQUENCE DESCRIPTION: SEQ ID NO:12:

Met Lys Gly Leu Ile Leu Val Gly Gly Tyr Gly Thr Arg Leu Arg Pro
1               5                   10                  15

Leu Thr Leu Thr Val Pro Lys Pro Leu Val Glu Phe Gly Asn Arg Pro
            20                  25                  30

Met Ile Leu His Gln Ile Glu Ala Leu Ala Asn Ala Gly Val Thr Asp
        35                  40                  45

Ile Val Leu Ala Val Asn Tyr Arg Pro Glu Val Met Val Glu Thr Leu
    50                  55                  60

Lys Lys Tyr Glu Lys Glu Tyr Gly Val Asn Ile Thr Phe Ser Val Glu
65              70                  75                  80

Thr Glu Pro Leu Gly Thr Ala Gly Pro Leu Lys Leu Ala Glu Asp Val
                85                  90                  95

Leu Lys Lys Asp Asn Ser Pro Phe Phe Val Leu Asn Ser Asp Val Ile
            100                 105                 110

Cys Glu Tyr Pro Phe Lys Glu Leu Ala Asp Phe His Lys Ala His Gly
        115                 120                 125

Gly Lys Gly Thr Ile Val Ala Thr Lys Val Asp Glu Pro Ser Lys Tyr
    130                 135                 140

Gly Val Ile Val His Asp Ile Ala Thr Pro Asn Leu Ile Asp Arg Phe
145                 150                 155                 160

Val Glu Lys Pro Lys Glu Phe Val Gly Asn Arg Ile Asn Ala Gly Leu
                165                 170                 175

Tyr Ile Leu Asn Pro Glu Val Ile Asp Leu Ile Glu Met Lys Pro Thr
            180                 185                 190

Ser Ile Glu Lys Glu Thr Phe Pro Ile Leu Val Glu Glu Lys Gln Leu
        195                 200                 205

Tyr Ser Phe Asp Leu Glu Gly Phe Trp Met Asp Val Gly Gln Pro Lys
    210                 215                 220

Asp Phe Leu Ser Gly Thr Val Leu Tyr Leu Asn Ser Leu Ala Lys Arg
225                 230                 235                 240

Gln Pro Lys Lys Leu Ala Thr Gly Ala Asn Ile Val Gly Asn Ala Leu
                245                 250                 255

Ile Asp Pro Thr Ala Lys Ile Ser Ser Thr Ala Lys Ile Gly Pro Asp
            260                 265                 270

Val Val Ile Gly Pro Asn Val Thr Ile Gly Asp Gly Val Arg Ile Thr
        275                 280                 285

Arg Ser Val Val Leu Cys Asn Ser Thr Ile Lys Asn His Ser Leu Val
    290                 295                 300

Lys Ser Thr Ile Val Gly Trp Asn Ser Thr Val Gly Gln Trp Cys Arg
305                 310                 315                 320

Leu Glu Gly Val Thr Val Leu Gly Asp Asp Val Glu Val Lys Asp Glu
                325                 330                 335

-continued

```
Ile Tyr Ile Asn Gly Gly Lys Val Leu Pro His Lys Ser Ile Ser Asp
            340             345             350

Asn Val Pro Lys Glu Ala Ile Ile Met
            355             360

(2) INFORMATION FOR SEQ ID NO:13:

(i) SEQUENCE CHARACTERISTICS:
        (A) LENGTH: 194 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 7345

(xi) SEQUENCE DESCRIPTION: SEQ ID NO:13:

Met Phe Asn Phe Lys Leu Val Leu Val Gly Pro Gly Gly Val Gly Lys
1               5                   10                  15

Ser Cys Leu Thr Ile Gln Phe Ile Ala Gln Lys Phe Val Asp Glu Tyr
                20                  25                  30

Asp Pro Thr Leu Glu Asp Ser Tyr Arg Lys Gln Thr Thr Val Asp Gly
            35                  40                  45

Glu Glu Cys Leu Leu Asp Ile Tyr Asp Thr Ala Gly Gln Glu Asp Phe
50                      55                  60

Ser Ala Val Arg Asp Gln Tyr Met Arg Thr Gly Glu Gly Phe Leu Cys
65                  70                  75                  80

Val Tyr Ser Ile Thr Tyr Leu Gln Ser Phe Lys Glu Ile His Arg Leu
                85                  90                  95

His Asn His Leu Leu Lys Val Lys Asp Leu Asp Ser Val Pro Phe Val
                100                 105                 110

Leu Val Gly Asn Lys Cys Asp Leu Asn Glu Tyr Arg Glu Val Ser Thr
                115                 120                 125

Ala Glu Gly Glu Glu Leu Ala Lys Lys Leu Asn Cys Lys Phe Leu Glu
            130                 135                 140

Thr Ser Ala Lys Glu Arg Ile Asn Val Ser Glu Ser Phe Tyr Glu Leu
145                 150                 155                 160

Val Arg Glu Val Lys Lys Ala Arg Gln Ser Asn Gln His Ser Asn Ser
                165                 170                 175

Gln Glu Gln Asn Thr Asp Gln Pro Ile Lys Lys Lys Ser Cys Asn
                180                 185                 190

Leu Leu
```

CELL CYCLE RELATED PROTEINS

FIELD OF THE INVENTION

This invention relates to nucleic acid and amino acid sequences of cell cycle related proteins and to the use of these sequences in the diagnosis, treatment, and prevention of cancer and immune disorders.

BACKGROUND OF THE INVENTION

Cell division is the fundamental process by which all living things grow and reproduce. In unicellular organisms such as yeast and bacteria, each cell division doubles the number of organisms, while in multicellular species many rounds of cell division are required to produce a new tissue or organ and to replace cells lost by wear or by programmed cell death. Details of the cell division cycle may vary, but the basic process consists of three principle events. The first event, interphase, involves preparations for cell division, replication of the DNA and production of essential proteins. In the second event, mitosis, the nuclear material is divided and separates to opposite sides of the cell. The final event, cytokinesis, is division and fission of the cell cytoplasm. The sequence and timing of these cell cycle events is under the control of the cell cycle control system which regulates the process at various check points. Over the past two decades, much research has been devoted to studying the structure and functions of various proteins that regulate these events.

The entry and exit of a cell from mitosis is regulated by the synthesis and destruction of a family of activating proteins called cyclins. Cyclins act by binding to and activating a group of cyclin-dependent protein kinases (Cdks) which then phosphorylate and activate selected proteins involved in the mitotic process. Several types of cyclins exist. (Ciechanover, A. (1994) Cell 79:13–21.) Two principle types are mitotic cyclin, or cyclin B, which controls entry of the cell into mitosis, and G1 cyclin, which controls events that drive the cell out of mitosis.

The activation and targeting of specific Cdks is also under control of certain cell division cycle (CDC) regulator proteins. For example in humans, CDC37 is a protein kinase-targeting subunit that binds and stabilizes Cdk4 and permits it to complex with cyclin D1. The formation of this complex is an important step for entry into the cell cycle. (Stepanova, L. et al. (1996) Genes and Development 10:1491–1502.)

Guanine nucleotide-binding proteins (GTP-binding proteins or G-proteins) also participate in cell cycle control as well as in a wide range of other regulatory functions including metabolism, growth, differentiation, signal transduction, cytoskeletal organization, and intracellular vesicle transport and secretion. G-proteins control a diverse set of regulatory pathways in response to hormones, growth factors, neuromodulators, or other signaling molecules. When these molecules bind to transmembrane receptors, signals are propagated to effector molecules by intracellular signal transducing proteins.

Some G-proteins are heterotrimeric, composed of Gα, Gβ, and Gγ subunits. (Watson, S. and Arkinstall, S. (1994) *The G-Protein Linked Receptor Facts Book*, pp. 296–314.) In these proteins, Gα binds to and hydrolyzes GTP resulting in the dissociation of Gα from a tightly complexed Gβγ dimer. The released Gα and Gβγ subunits in turn regulate the activity of effector proteins such as cGMP phosphodiesterase and adenyl cyclase. (Watson, J. A. et al. (1996) J. Biol. Chem. 271:28154–28160.) The low molecular weight (LMW) GTP-binding proteins are another class of G-proteins which consist of single polypeptides of 21–30 kDa. These proteins regulate cell growth, cell cycle control, protein secretion, and intracellular vesicle interaction. LMW GTP-binding proteins activate cellular proteins by transducing mitogenic signals in response to extracellular signals from receptors. (Tavitian, A. (1995) C. R. Seances Soc. Biol. Fil. 189:7–12.) During this process, the hydrolysis of GTP acts as an energy source as well as an on-off switch for the GTPase activity of the LMW GTP-binding proteins.

The LMW GTP-binding proteins have been grouped into four subfamilies: Ras, Rho, Rab and Ran. Specifically, Ras genes are essential in the control of cell proliferation and mutant Ras genes have been associated with cancer; Rho proteins control signal transduction in the process of linking receptors of growth factors to actin polymerization which is necessary for cell division; Rab proteins control the translocation of vesicles to and from membranes for protein localization, protein processing, and secretion; and Ran proteins are located in the cell nucleus and have a key role in nuclear protein import, control of DNA synthesis, and cell-cycle progression.

Cell cycle progression also requires co-ordinate expression of certain other proteins as well. N-glycosylation of proteins is required for progression through the G1 period of interphase. In yeast, for example, PSAL is an essential gene for G1 progression that encodes a protein with homology to NDP-hexose pyrophosphorylase; an enzyme that catalyzes the formation of activated sugar nucleotides. (Benton, B. K. et al. (1996) Curr. Genet. 29:106–113.) PSA1 appears to play a role in N-glycosylation and Gi progression perhaps by responding to levels of glycosylation necessary for G1 progression. Inhibitors of N-glycosylation, such as tunicamycin, induce G1 arrest in mammalian cells as well as yeast, suggesting that this mechanism is evolutionarily conserved in all eukaroytes. (Benton et al. supra.)

The discovery of new cell cycle related proteins and the polynucleotides encoding them satisfies a need in the art by providing new compositions which are useful in the diagnosis, treatment, and prevention of cancer and immune disorders.

SUMMARY OF THE INVENTION

The invention features substantially purified polypeptides, cell cycle related proteins, referred to collectively as "CCRP" and individually as "CCRP-1", "CCRP-2", "CCRP-3", "CCRP-4", and "CCRP-5". In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5.

The invention further provides a substantially purified variant having at least 90% amino acid identity to the amino acid sequences of SEQ ID NO:1, SEQ ID NO:2, SEQ ID NO:3, SEQ ID NO:4, or SEQ ID NO:5, or to a fragment of any of these sequences. The invention also provides an isolated and purified polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5. The invention also includes an isolated and purified polynucleotide variant having at least 90% polynucleotide seqeunce identity to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5, as well as an isolated and purified polynucleotide having a sequence which is complementary to the polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5.

The invention also provides an isolated and purified polynucleotide comprising a polynucleotide sequence selected from the group consisting of SEQ ID NO:6, SEQ ID NO:7, SEQ ID NO:8, SEQ ID NO:9, SEQ ID NO:10, a fragment of SEQ ID NO:6, a fragment of SEQ ID NO:7, a fragment of SEQ ID NO:8, a fragment of SEQ ID NO:9, and a fragment of SEQ ID NO:10. The invention further provides an isolated and purified polynucleotide variant having at least 90% polynucleotide sequence identity to the polynucleotide sequence comprising a polynucleotide sequence selected from the group consisting of SEQ ID NO:6, SEQ ID NO:7, SEQ ID NO:8, SEQ ID NO:9, SEQ ID NO:10, a fragment of SEQ ID NO:6, a fragment of SEQ ID NO:7, a fragment of SEQ ID NO:8, a fragment of SEQ ID NO:9, and a fragment of SEQ ID NO:10, as well as an isolated and purified polynucleotide having a sequence which is complementary to the polynucleotide comprising a polynucleotide sequence selected from the group consisting of SEQ ID NO:6, SEQ ID NO:7, SEQ ID NO:8, SEQ ID NO:9, SEQ ID NO:10, a fragment of SEQ ID NO:6, a fragment of SEQ ID NO:7, a fragment of SEQ ID NO:8, a fragment of SEQ ID NO:9, and a fragment of SEQ ID NO:10.

The invention further provides an expression vector containing at least a fragment of the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5. In another aspect, the expression vector is contained within a host cell.

The invention also provides a method for producing a polypeptide comprising the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5 in conjunction with a suitable pharmaceutical carrier.

The invention further includes a purified antibody which binds to a polypeptide comprising the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5, as well as a purified agonist and a purified antagonist to the polypeptide.

The invention also provides a method for treating or preventing a cancer, the method comprising administering to a subject in need of such treatment an effective amount of an antagonist of the polypeptide having an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5.

The invention also provides a method for treating or preventing an immune disorder, the method comprising administering to a subject in need of such treatment an effective amount of an antagonist of the polypeptide having an amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5.

The invention also provides a method for detecting a polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, SEQ ID NO:3, SEQ ID NO:4, SEQ ID NO:5, a fragment of SEQ ID NO:1, a fragment of SEQ ID NO:2, a fragment of SEQ ID NO:3, a fragment of SEQ ID NO:4, and a fragment of SEQ ID NO:5 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

BRIEF DESCRIPTION OF THE FIGURES

FIGS. 1A and 1B show the amino acid sequence alignments between CCRP-2 (680517; SEQ ID NO:2), and a human CDC37 homolog (GI 1375485; SEQ ID NO:11), produced using the multisequence alignment program of LASERGENE software (DNASTAR Inc., Madison, Wis.).

FIGS. 2A and 2B show the amino acid sequence alignments between CCRP-3 (1693222; SEQ ID NO:3), and a putative NDP-hexose pyrophosphorylase from yeast, PSAL (GI 1292898; SEQ ID NO:12), produced using the multisequence alignment program of LASERGENE software.

FIG. 3 shows the amino acid sequence alignments between CCRP-5 (2666519; SEQ ID NO:5), and a Ras-related GTP-binding protein from *Dictyostelium discoideum* (GI 7345; SEQ ID NO:13), produced using the multisequence alignment program of LASERGENE software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"CCRP," as used herein, refers to the amino acid sequences of substantially purified CCRP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to CCRP, increases or prolongs the duration of the effect of CCRP. Agonists may include proteins, nucleic acids, carbohydrates, or any other molecules which bind to and modulate the effect of CCRP.

An "allele" or an "allelic sequence," as these terms are used herein, is an alternative form of the gene encoding CCRP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding CCRP, as described herein, include those sequences with deletions, insertions, or substitutions of different nucleotides, resulting in a polynucleotide the same CCRP or a polypeptide with at least one functional characteristic of CCRP. Included within this definition are polymorphisms which may or may not be readily detectable using a particular oligonucleotide probe of the polynucleotide encoding CCRP, and improper or unexpected hybridization to alleles, with a locus other than the normal chromosomal locus for the polynucleotide sequence encoding CCRP. The encoded protein may also be "altered," and may contain deletions, insertions, or substitutions of amino acid residues which produce a silent change and result in a functionally equivalent CCRP. Deliberate amino acid substitutions may be made on the basis of similarity in polarity, charge, solubility, hydrophobicity, hydrophilicity, and/or the amphipathic nature of the residues, as long as the biological or immunological activity of CCRP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of CCRP which are preferably about 5 to about 15 amino acids in length and which retain some biological activity or immunological activity of CCRP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to CCRP, decreases the amount or the duration of the effect of the biological or immunological activity of CCRP. Antagonists may include proteins, nucleic acids, carbohydrates, antibodies, or any other molecules which decrease the effect of CCRP.

As used herein, the term "antibody" refers to intact molecules as well as to fragments thereof, such as Fab, F(ab')$_2$, and Fv fragments, which are capable of binding the epitopic determinant. Antibodies that bind CCRP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic CCRP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding CCRP or fragments of CCRP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding CCRP, by northern analysis is indicative of the presence of nucleic acids encoding CCRP in a sample, and thereby correlates with expression of the transcript from the polynucleotide encoding CCRP.

A "deletion," as the term is used herein, refers to a change in the amino acid or nucleotide sequence that results in the absence of one or more amino acid residues or nucleotides.

The term "derivative," as used herein, refers to the chemical modification of CCRP, of a polynucleotide sequence encoding CCRP, or of a polynucleotide sequence complementary to a polynucleotide sequence encoding CCRP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non- specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison, Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat. Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of CCRP. For example, modulation may cause an increase or a decrease in protein activity, binding characteristics, or any other biological, functional, or immunological properties of CCRP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding CCRP, or fragments thereof, or CCRP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5X SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of CCRP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of new human cell cycle related proteins (CCRP), the polynucleotides encoding CCRP, and the use of these compositions for the diagnosis, treatment, or prevention of cancer and immune disorders. Table 1 shows the sequence identification numbers, Incyte Clone identification number, and cDNA library for each of the human cell cycle related proteins disclosed herein.

| PROTEIN | NUCLEOTIDE | CLONE ID | LIBRARY |
| --- | --- | --- | --- |
| SEQ ID NO:1 | SEQ ID NO:6 | 78191 | SYNORAB01 |
| SEQ ID NO:2 | SEQ ID NO:7 | 680517 | UTRSNOT02 |
| SEQ ID NO:3 | SEQ ID NO:8 | 1693222 | COLNNOT23 |
| SEQ ID NO:4 | SEQ ID NO:9 | 2522306 | BRAITUT21 |
| SEQ ID NO:5 | SEQ ID NO:10 | 2666519 | PENCNOT01 |

Nucleic acids encoding the CCRP-1 of the present invention were first identified in Incyte Clone 78191 from the synovial membrane tissue cDNA library (SYNORAB01) using a computer search for amino acid sequence alignments. A consensus sequence, SEQ ID NO:6, was derived from the following overlapping and/or extended nucleic acid sequences: Incyte Clones 078191 (SYNORAB01), 1959181 (CONNNOT01), and shotgun sequences SBLA03486F, SBLA03727, SBLA00692, SBLA02812, SBLA01357, and SBLA00411.

In one embodiment, the invention encompasses a polypeptide comprising the amino acid sequence of SEQ ID NO:1. CCRP-1 is 395 amino acids in length and has a potential N-glycosylation site at residue N51, various potential phosphorylation sites for cAMP- and cGMP-dependent protein kinase at S190, for casein kinase II at S22, T23, S59, S123, T137, T204, S298, and S329, for protein kinase C at S56, S63, T97, T100, T137, S286, T304, S336, T372, and T390, and for tyrosine kinase at Y319. CCRP-1 also has a Beta-transducin (Gβ) family Trp-Asp repeats signature motif, in three sequences found between residues I120 and S134, I210 and V224, and L340 and V354. A fragment of SEQ ID NO:6 from about nucleotide 121 to about nucleotide 192 is useful for hybridization. Northern analysis shows the expression of this sequence in various libraries, at least 21% of which are immortalized or cancerous and at least 37% of which involve immune response. Of particular note is the expression of CCRP-1 in nervous system and male and female reproductive cDNA libraries.

Nucleic acids encoding the CCRP-2 of the present invention were first identified in Incyte Clone 680517 from the uterine tissue cDNA library (UTRSNOT02) using a computer search for amino acid sequence alignments. A consensus sequence, SEQ ID NO:7, was derived from the following overlapping and/or extended nucleic acid sequences: Incyte Clones 087436 (LIVRNOT01), 680517 (UTRSNOT02), 1305760 (PLACNOT02), 1642890 (HEARFET01), 1773041 (MENTUNON3), 1962527 (BRSTNOT04), 2448614 (THP1NOT03), 2972709 (HEAONOT02), and 3768624 (BRSTNOT24).

In another embodiment, the invention encompasses a polypeptide comprising the amino acid sequence of SEQ ID NO:2. CCRP-2 is 337 amino acids in length and has a potential N-glycosylation site at residue N137, and potential phosphorylation sites for cAMP- and cGMP-dependent protein kinase at T149, for casein kinase II at S24, T149, and S173, for protein kinase C at S32, S178, and T193, and for tyrosine kinase at Y187 and Y255. As shown in FIGS. 1A and 1B, CCRP-2 has chemical and structural homology with the human CDC37 homolog (GI 1375485: SEQ ID NO:11). In particular CCRP-2 and human CDC37 share 34% identity. A fragment of SEQ ID NO:7 from about nucleotide 405 to about nucleotide 479 is useful for hybridization. Northern analysis shows the expression of this sequence in various libraries, at least 43% of which are immortalized or cancerous, and at least 39% of which involve immune response. Of particular note is the expression of CCRP-2 in male and female reproductive, nervous system, hematopoietic, and gastrointestinal cDNA libraries.

Nucleic acids encoding the CCRP-3 of the present invention were first identified in Incyte Clone 1693222 from the diseased colon tissue cDNA library (COLNNOT23) using a computer search for amino acid sequence alignments. A consensus sequence, SEQ ID NO:8, was derived from the following overlapping and/or extended nucleic acid sequences: Incyte Clones 795172 (OVARNOT03), 1266934 (BRAINOT09), 1307552 (COLNFET02),1547117 (PROSTUT04), 1693222 (COLNNOT23), and 2204091 (SPLNFET02).

In another embodiment, the invention encompasses a polypeptide comprising the amino acid sequence of SEQ ID NO:3. CCRP-3 is 422 amino acids in length and has a potential N-glycosylation site at residue N145, and potential phosphorylation sites for casein kinase II at T268, S325, and T364, and for protein kinase C at T219, S320, S333, T371, and S375. As shown in FIGS. 2A and 2B, CCRP-3 has chemical and structural homology with a putative NDP-hexose pyrophosphorylase from yeast, PSAL (GI 1292898; SEQ ID NO:12). In particular, CCRP-3 and yeast PSA1 share 19% homology. A fragment of SEQ ID NO:8 from about nucleotide 314 to about nucleotide 400 is useful for hybridization. Northern analysis shows the expression of this sequence in various libraries, at least 54% of which are immortalized or cancerous, and at least 28% involve immune response. Of particular note is the expression of CCRP-3 in cancers of the prostate, mesentery, adrenals, pancreas, lung, breast, and brain, and in inflammatory conditions including rheumatoid arthritis, lymphocytic thyroiditis, splenomegaly, cholecystitis, and ulcerative colitis.

Nucleic acids encoding the CCRP-4 of the present invention were first identified in Incyte Clone 2522306 from the brain tumor cDNA library (BRAITUT21) using a computer search for amino acid sequence alignments. A consensus sequence, SEQ ID NO:9, was derived from the following overlapping and/or extended nucleic acid sequences: Incyte Clones 2522306 (BRAITUT21), 3121261 and 3124505 (LNODNOT05), 3339573 (SPLNNOT10), and shotgun sequences SAEA00921 and SAEA00972.

In another embodiment, the invention encompasses a polypeptide comprising the amino acid sequence of SEQ ID NO:4. CCRP-4 is 367 amino acids in length and has a potential signal peptide sequence from residue Ml to R17, a potential amidation site at R243, and a potential glycosaminoglycan attachment site at S34. Potential protein phosphorylation sites are found for cAMP- and cGMP-dependent protein kinase at S248, for casein kinase II at T86, S206, and S315, for protein kinase C at S19, S60, and T329, and for tyrosine kinase at Y199. A potential ATP/GTP-binding site motif A (P-loop) is found in the sequence G32 through S39. CCRP-4 has chemical and structural homology with a human cell division control (CDC) protein (GI 1809317). In particular, CCRP-4 and the human CDC protein share 61 % homology. A fragment of SEQ ID NO:9 from about nucleotide 326 to about nucleotide 380 is useful for hybridization. Northern analysis shows the expression of this sequence in various libraries, at least 42% of which are immortalized or cancerous, and at least 46% of which involve immune response. Of particular note is the expression of CCRP-4 in leukemia, uterine, lung, and brain tumors, and in inflammatory conditions (lymphocytic thyroiditis and splenomegaly).

Nucleic acids encoding the CCRP-5 of the present invention were first identified in Incyte Clone 2666519 from the penis corpus cavernosum cDNA library (PENCNOT01) using a computer search for amino acid sequence alignments. A consensus sequence, SEQ ID NO:10, was derived from the following overlapping and/or extended nucleic acid sequences: Incyte Clones 2666519 (PENCNOT01) and shotgun sequences SBLA03507 and SBLA03125.

In another embodiment, the invention encompasses a polypeptide comprising the amino acid sequence of SEQ ID NO:5. CCRP-5 is 217 amino acids in length and has a potential ATP/GTP-binding site motif A (P-loop) in the sequence G9 through S16, and potential phosphorylation sites for cAMP- and cGMP-dependent protein kinase at S185, for casein kinase II at S89, T91, and S152, and for protein kinase C at T24, T35, S98, and S207. As shown in FIG. 3, CCRP-5 has chemical and structural homology with a Ras-related, GTP-binding protein from *D. discoideum* (GI 7345; SEQ ID NO:13) In particular, CCRP-5 and the Ras-related protein share 29% homology, the ATP/GTP-binding site motif, and the potential phosphorylation site at S152 in CCRP-5. A fragment of SEQ ID NO:10 from about nucleotide 169 to about nucleotide 216 is useful for hybridization. Northern analysis shows the expression of this sequence in various libraries, at least 20% of which are immortalized or cancerous. Of particular note is the expression of CCRP-5 in gastrointestinal tissues (60%).

The invention also encompasses CCRP variants. A preferred CCRP variant is one which has at least about 80%, more preferably at least about 90%, and most preferably at least about 95% amino acid sequence identity to the CCRP amino acid sequence, and which contains at least one functional or structural characteristic of CCRP.

The invention also encompasses polynucleotides which encode CCRP. In a particular embodiment, the invention encompasses a polynucleotide sequence comprising a sequence selected from the group consisting of SEQ ID NO:6, SEQ ID NO:7, SEQ ID NO:8, SEQ ID NO:9, and SEQ ID NO:10, which encodes an CCRP.

The invention also encompasses a variant of a polynucleotide sequence encoding CCRP. In particular, such a variant polynucleotide sequence will have at least about 80%, more preferably at least about 90%, and most preferably at least about 95% polynucleotide sequence identity to the polynucleotide sequence encoding CCRP. A particular aspect of the invention encompasses a variant of a polynucleotide sequence selected from the group consisting of SEQ ID NO:6, SEQ ID NO:7, SEQ ID NO:8, SEQ ID NO:9, and SEQ ID NO:10 which has at least about 80%, more preferably at least about 90%, and most preferably at least about 95% polynucleotide sequence identity to a polynucleotide sequence selected from the group consisting of SEQ ID NO:6, SEQ ID NO:7, SEQ ID NO:8, SEQ ID NO:9, and SEQ ID NO:10. Any one of the polynucleotide variants described above can encode an amino acid sequence which contains at least one functional or structural characteristic of CCRP.

It will be appreciated by those skilled in the art that as a result of the degeneracy of the genetic code, a multitude of polynucleotide sequences encoding CCRP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring CCRP, and all such variations are to be considered as being specifically disclosed.

Although nucleotide sequences which encode CCRP and its variants are preferably capable of hybridizing to the nucleotide sequence of the naturally occurring CCRP under appropriately selected conditions of stringency, it may be advantageous to produce nucleotide sequences encoding CCRP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding CCRP and its derivatives without altering the encoded amino acid sequences include the production of RNA transcripts having more desirable properties, such as a greater half-life, than transcripts produced from the naturally occurring sequence.

The invention also encompasses production of DNA sequences which encode CCRP and CCRP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding CCRP or any fragment thereof.

Also encompassed by the invention are polynucleotide sequences that are capable of hybridizing to the claimed polynucleotide sequences, and, in particular, to those shown in SEQ ID NO:6, SEQ ID NO:7, SEQ ID NO:8, SEQ ID NO:9, SEQ ID NO:10, a fragment of SEQ ID NO:6, a fragment of SEQ ID NO:7, a fragment of SEQ ID NO:8, a fragment of SEQ ID NO:9, and a fragment of SEQ ID NO:10 under various conditions of stringency. (See, e.g., Wahl, G. M. and S. L. Berger (1987) Methods Enzymol. 152:399–407; Kimmel, A. R. (1987) Methods Enzymol. 152:507–51 1.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio.), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL, Gaithersburg, Md.). Preferably, the process is automated with machines such as the MICROLAB 2200 (Hamilton, Reno, Nav.), Peltier thermal cycler (PTC200; MJ Research, Watertown, Mass.), and the ABI CATALYST and 373 and 377 DNA sequencers (Perkin Elmer).

The nucleic acid sequences encoding CCRP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequenc. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode CCRP may be used in recombinant DNA molecules to direct expression of CCRP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express CCRP.

As will be understood by those of skill in the art, it may be advantageous to produce CCRP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter CCRP-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding CCRP may be ligated to a heterologous sequence to encode a fusion protein. For example, to screen peptide libraries for inhibitors of CCRP activity, it may be useful to encode a chimeric CCRP protein that can be recognized by a commercially available antibody. A fusion protein may also be engineered to contain a cleavage site located between the CCRP encoding sequence and the heterologous protein sequence, so that CCRP may be cleaved and purified away from the heterologous moiety.

In another embodiment, sequences encoding CCRP may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.)

Alternatively, the protein itself may be produced using chemical methods to synthesize the amino acid sequence of CCRP, or a fragment thereof. For example, peptide synthesis can be performed using various solid-phase techniques. (See, e.g., Roberge, J. Y. et al. (1995) Science 269:202–204.) Automated synthesis may be achieved using the ABI 431 A peptide synthesizer (Perkin Elmer). Additionally, the amino acid sequence of CCRP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active CCRP, the nucleotide sequences encoding CCRP or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding CCRP and appropriate transcriptional and translational control elements. These methods include in vitro recombinant DNA techniques, synthetic techniques, and in vivo genetic recombination. (See, e.g., Sambrook, J. et al. (1989) *Molecular Cloning A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding CCRP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding CCRP which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the BLUESCRIPT phagemid (Stratagene, La Jolla, Calif.) or PSPORT1 plasmid (GIBco/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding CCRP, vectors based on SV40 or EBV may be used with an appropriate selectable marker.

In bacterial systems, a number of expression vectors may be selected depending upon the use intended for CCRP. For example, when large quantities of CCRP are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding CCRP may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Amersham Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomvces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding CCRP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express CCRP. For example, in one such system, *Autographa californica* nuclear polyhedrosis virus (AcNPV) is used as a vector to express foreign genes in *Spodoptera frugiperda* cells or in Trichoplusia larvae. The sequences encoding CCRP may be cloned into a non-essential region of the virus, such as the polyhedrin gene, and placed under control of the polyhedrin promoter. Successful insertion of sequences encoding CCRP will render the polyhedrin gene inactive and produce recombinant virus lacking coat protein. The recombinant viruses may then be used to infect, for example, *S. frugiperda* cells or Trichoplusia larvae in which CCRP may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding CCRP may be ligated into an adenovirus transcription/translation complex consisting of the late promoter and tripartite leader sequence. Insertion in a non-essential E1 or E3 region of the viral genome may be used to obtain a viable virus which is capable of expressing CCRP in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding CCRP. Such signals include the ATG initiation codon and adjacent sequences. In cases where sequences encoding CCRP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing CCRP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in $tk^-$ or $apr^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als and pat confer resistance to chlorsulfuron and phosphinotricin acetyltransferase, respectively. (See, e.g., Wigler, M. et al. (1980) Proc. Nati. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding CCRP is inserted within a marker gene sequence, transformed cells containing sequences encoding CCRP can be identified by the absence of marker gene function. Alternatively, a marker gene can be placed in tandem with a sequence encoding CCRP under the control of a single promoter. Expression of the marker gene in response to induction or selection usually indicates expression of the tandem gene as well.

Alternatively, host cells which contain the nucleic acid sequence encoding CCRP and express CCRP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding CCRP can be detected by DNA-DNA or DNA-RNA hybridization or amplification using probes or fragments or fragments of polynucleotides encoding CCRP. Nucleic acid amplification based assays involve the use of oligonucleotides or oligomers based on the sequences encoding CCRP to detect transfornants containing DNA or RNA encoding CCRP.

A variety of protocols for detecting and measuring the expression of CCRP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on CCRP is preferred, but a competitive binding assay may be employed. These and other assays are well described in the art. (See, e.g., Hampton, R. et al. (1990) *Serological Methods, a Laboratory Manual*, APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding CCRP include oligolabeling, nick translation, end-labeling, or PCR amplification using a labeled nucleotide. Alternatively, the sequences encoding CCRP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding CCRP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode CCRP may be designed to contain signal sequences which direct secretion of CCRP through a prokaryotic or eukaryotic cell membrane. Other constructions may be used to join sequences encoding CCRP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAG extension/affinity purification system (Immunex Corp., Seattle, Wash.). The inclusion of cleavable linker sequences, such as those specific for Factor XA or enterokinase (Invitrogen, San Diego, Calif.), between the purification domain and the CCRP encoding sequence may be used to facilitate purification. One such expression vector provides for expression of a fusion protein containing CCRP and a nucleic acid encoding 6 histidine residues preceding a thioredoxin or an enterokinase cleavage site. The histidine residues facilitate purification on immobilized metal ion affinity chromatography (IMIAC). (See, e.g., Porath, J. et al. (1992) Prot. Exp. Purif. 3: 263–281.) The enterokinase cleavage site provides a means for purifying CCRP from the fusion protein. (See, e.g., Kroll, D. J. et al. (1993) DNA Cell Biol. 12:441–453.)

Fragments of CCRP may be produced not only by recombinant production, but also by direct peptide synthesis using solid-phase techniques. (See, e.g., Creighton, supra.) Protein synthesis may be performed by manual techniques or by automation. Automated synthesis may be achieved, for example, using the Applied Biosystems 431 A peptide synthesizer (Perkin Elmer). Various fragments of CCRP may be synthesized separately and then combined to produce the full length molecule.

THERAPEUTICS

Chemical and structural homology exists among CCRP and a human CDC37 homolog (GI 1375485), a putative NDP-hexose pyrophosphorylase from yeast (GI 1292898), Ras-related GTP-binding protein from *D. discoideum* (GI 7345), and a human CDC related protein (GI 1809317). In addition, CCRP is expressed in cancerous tissues and immortalized cell lines and tissues associated with inflammation and the immune response. Therefore, CCRP appears to play a role in cancer and immune disorders.

Therefore, in one embodiment, an antagonist of CCRP may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds CCRP may be used directly as an antagonist or indirectly as a targeting or delivery mechanism for bringing a pharmaceutical agent to cells or tissue which express CCRP.

In an additional embodiment, a vector expressing the complement of the polynucleotide encoding CCRP may be administered to a subject to treat or prevent a cancer including, but not limited to, those described above.

In another embodiment, an antagonist of CCRP may be administered to a subject to treat or prevent an immune disorder. Such a disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis ,bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In an additional embodiment, a vector expressing the complement of the polynucleotide encoding CCRP may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of CCRP may be produced using methods which are generally known in the art. In particular, purified CCRP may be used to produce antibodies or to screen libraries of pharmaceutical agents to identify those which specifically bind CCRP. Antibodies to CCRP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with CCRP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to CCRP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of CCRP amino acids may be fused with those of another protein, such as KLH, and antibodies to the chimeric molecule may be produced.

Monoclonal antibodies to CCRP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.) In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce CCRP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for CCRP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between CCRP and its specific antibody. A two-site, monoclonal-based immunoassay utilizing monoclonal antibodies reactive to two non-interfering CCRP epitopes is preferred, but a competitive binding assay may also be employed. (Maddox, supra.)

In another embodiment of the invention, the polynucleotides encoding CCRP, or any fragment or complement thereof, may be used for therapeutic purposes. In one aspect, the complement of the polynucleotide encoding CCRP may be used in situations in which it would be desirable to block the transcription of the mRNA. In particular, cells may be transformed with sequences complementary to polynucleotides encoding CCRP. Thus, complementary molecules or fragments may be used to modulate CCRP activity, or to achieve regulation of gene function. Such technology is now well known in the art, and sense or antisense oligonucleotides or larger fragments can be designed from various locations along the coding or control regions of sequences encoding CCRP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding CCRP. (See, e.g., Sambrook, supra; and Ausubel, supra.)

Genes encoding CCRP can be turned off by transforming a cell or tissue with expression vectors which express high levels of a polynucleotide, or fragment thereof, encoding CCRP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding CCRP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding CCRP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding CCRP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of CCRP, antibodies to CCRP, and mimetics, agonists, antagonists, or inhibitors of CCRP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of CCRP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example CCRP or fragments thereof, antibodies of CCRP, and agonists, antagonists or inhibitors of CCRP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind CCRP may be used for the diagnosis of disorders characterized by expression of CCRP, or in assays to monitor patients being treated with CCRP or agonists, antagonists, or inhibitors of CCRP. Antibodies useful for diagnostic purposes may be prepared in the same manner as described above for therapeutics. Diagnostic assays for CCRP include methods which utilize the antibody and a label to detect CCRP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring CCRP, including ELISAs, RIAs, and FACS, are known in the art and provide a basis for diagnosing altered or abnormal levels of CCRP expression. Normal or standard values for CCRP expression are established by combining body fluids or cell extracts taken from normal mammalian subjects, preferably human, with antibody to CCRP under conditions suitable for complex formation The amount of standard complex formation may be quantitated by various methods, preferably by photometric means. Quantities of CCRP expressed in subject samples from biopsied tissues are compared with the standard values. Deviation between standard and subject values establishes the parameters for diagnosing disease.

In another embodiment of the invention, the polynucleotides encoding CCRP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of CCRP may be correlated with disease. The diagnostic assay may be used to determine absence, presence, and excess expression of CCRP, and to monitor regulation of CCRP levels during therapeutic intervention.

In one aspect, hybridization with PCR probes which are capable of detecting polynucleotide sequences, including genomic sequences, encoding CCRP or closely related molecules may be used to identify nucleic acid sequences which encode CCRP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding CCRP, alleles, or related sequences.

Probes may also be used for the detection of related sequences, and should preferably have at least 50% sequence identity to any of the CCRP encoding sequences. The hybridization probes of the subject invention may be DNA or RNA and may be derived from the sequence of SEQ ID NO:6, SEQ ID NO:7, SEQ ID NO:8, SEQ ID NO:9, or SEQ ID NO:10 or from genomic sequences including promoters, enhancers, and introns of the CCRP gene.

Means for producing specific hybridization probes for DNAs encoding CCRP include the cloning of polynucleotide sequences encoding CCRP or CCRP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$p or $^{35}$S, or by enzymatic labels, such as alkaline phosphatase coupled to the probe via avidin/biotin coupling systems, and the like.

Polynucleotide sequences encoding CCRP may be used for the diagnosis of a disorder associated with expression of CCRP. Examples of such a disorder include, but are not limited to, cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis ,bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding CCRP may be used in Southern or northern analysis, dot blot, or other membrane-based technologies; in PCR technologies; in dipstick, pin, and ELISA assays; and in microarrays utilizing fluids or tissues from patients to detect altered CCRP expression. Such qualitative or quantitative methods are well known in the art.

In a particular aspect, the nucleotide sequences encoding CCRP may be useful in assays that detect the presence of associated disorders, particularly those mentioned above. The nucleotide sequences encoding CCRP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding CCRP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of CCRP, a normal or standard profile for expression is established. This may be accomplished by combining body fluids or cell extracts taken from normal subjects, either animal or human, with a sequence, or a fragment thereof, encoding CCRP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding CCRP may involve the use of PCR. These oligomers may be chemically synthesized, generated enzymatically, or produced in vitro. Oligomers will preferably contain a fragment of a polynucleotide encoding CCRP, or a fragment of a polynucleotide complementary to the polynucleotide encoding CCRP, and will be employed under optimized conditions for identification of a specific gene or condition. Oligomers may also be employed under less stringent conditions for detection or quantitation of closely related DNA or RNA sequences.

Methods which may also be used to quantitate the expression of CCRP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 219:229.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1 996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding CCRP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding CCRP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, CCRP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between CCRP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with CCRP, or fragments thereof, and washed. Bound CCRP is then detected by methods well known in the art. Purified CCRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding CCRP specifically compete with a test compound for binding CCRP. In this manner, antibodies can be used to detect the presence of any peptide which shares one or more antigenic determinants with CCRP.

In additional embodiments, the nucleotide sequences which encode CCRP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. BRAITUT21 cDNA Library Construction

The BRAITUT21 cDNA library was constructed from cancerous brain tissue obtained from a 61-year-old female during a cerebral meningeal excision. Pathology indicated subfrontal meningothelial meningioma with no atypia. Analysis of ethmoid tissue and mucosal tissue indicated meningioma. The patient presented with headache, an unspecified form of epilepsy, and a disturbance of sensation of smell and taste. Patient history included hyperlipidemia, depressive disorder, irritable bowel, skin cancer of the leg, and fibromyalgia.

The frozen tissue was homogenized and lysed in TRIZOL reagent (1 gm tissue/I 0 ml TRIZOL; Cat. #10296–028; Gibco/BRL) using a Polytron PT-3000 homogenizer (Brinkmann Instruments, Westbury, N.Y.). After a brief incubation on ice, chloroform was added (1:5 v/v), and the lysate was centrifuged. The aqueous layer was removed to a fresh tube, and the RNA extracted with isopropanol, resuspended in DEPC-treated water, and DNase treated for 25 min at 37° C. The RNA was re-extracted once with acid phenol- chloroform pH 4.7 and precipitated using 0.3 M sodium acetate and 2.5 volumes ethanol. The mRNAs were isolated using the OLIGOTEX kit (QIAGEN, Inc., Chatsworth, Calif.) and used to construct the cDNA library.

The mRNA was handled according to the recommended protocols in the SUPERSCRIPT plasmid system for cDNA synthesis and plasmid cloning (Cat. #18248-013, Gibco/BRL). The cDNAs were fractionated on a SEPHAROSE CL4B column (Cat. #275105-01; Pharmacia), and those cDNAs exceeding 400 bp were ligated into pINCY 1. The plasmid pINCY 1 was subsequently transformed into DH5α competent cells (Cat. #18258-012; Gibco/BRL).

II. Isolation and Sequencing of cDNA Clones

Plasmid DNA was released from the cells and purified using the R.E.A.L. PREP 96 plasmid kit (Catalog #26173; QIAGEN, Inc.). The recommended protocol was employed except for the following changes: 1) the bacteria were cultured in I ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton MICROLAB 2200 (Hamilton, Reno, Nev.) in combination with Peltier thermal cyclers (PTC200 from MJ Research, Watertown, Mass.) and ABI 377 DNA sequencing systems.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol. 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1 992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam). Deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1 997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

% sequence identity x % maximum BLAST score 100

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding CCRP occurs. Abundance and percent abundance are also reported. Abundance directly reflects the number of times a particular transcript is represented in a cDNA library, and percent abundance is abundance divided by the total number of sequences examined in the cDNA library.

V. Extension of CCRP Encoding Polynucleotides

The nucleic acid sequences of Incyte Clones 78191, 680517, 1693222, 2522306, and 2666519 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences, Plymouth, Minn.), or another appropriate program, to be about 22 to 30 nucleotides in length, to have a GC content of about 50% or more, and to anneal to the target sequence at temperatures of about 68 ° C. to about 72 ° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M.J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μT4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:6, SEQ ID NO:7, SEQ ID NO:8, SEQ ID NO:9, and SEQ ID NO:10 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:6, SEQ ID NO:7, SEQ ID NO:8, SEQ ID NO:9, and SEQ ID NO:10 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN, Boston, Mass.). The labeled oligonucleotides are substantially purified using a SEPHADEX G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN, Boston, Mass.).

The DNA from each digest is fractionated on a 0.7 percent agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed, and a scanner is used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the CCRP-encoding sequences, or any parts thereof, are used to detect, decrease, or inhibit expression of naturally occurring CCRP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of CCRP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the CCRP-encoding transcript.

IX. Expression of CCRP

Expression of CCRP is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101: 123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of CCRP into bacterial growth media which can be used directly in the following assay for activity.

X. Demonstration of CCRP Activity

CCRP activity is demonstrated by its effect on mitosis in quiescent cells transfected with cDNA encoding CCRP. CCRP is expressed by transforming a mammalian cell line such as COS7, HeLa or CHO with an eukaryotic expression vector encoding CCRP. Eukaryotic expression vectors are commercially available, and the techniques to introduce them into cells are well known to those skilled in the art. The cells are incubated for 48–72 hours after transformation under conditions appropriate for the cell line to allow expression of CCRP. Phase microscopy is used to compare the mitotic index of transformed versus control cells. The increase in the mitotic index is proportional to the activity of CCRP in the transformed cells.

XI. Production of CCRP Specific Antibodies

CCRP substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the CCRP amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring CCRP Using Specific Antibodies

Naturally occurring or recombinant CCRP is substantially purified by immunoaffinity chromatography using antibodies specific for CCRP. An immunoaffinity column is constructed by covalently coupling anti-CCRP antibody to an activated chromatographic resin, such as CNBr-activated SEPHAROSE (Pharmacia & Upjohn). After the coupling, the resin is blocked and washed according to the manufacturer's instructions.

Media containing CCRP are passed over the immunoaffinity column, and the column is washed under conditions that allow the preferential absorbance of CCRP (e.g., high ionic strength buffers in the presence of detergent). The column is eluted under conditions that disrupt antibody/CCRP binding (e.g., a buffer of pH 2 to pH 3, or a high concentration of a chaotrope, such as urea or thiocyanate ion), and CCRP is collected.

XIII. Identification of Molecules Which Interact with CCRP

CCRP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled CCRP, washed, and any wells with labeled CCRP complex are assayed. Data obtained using different concentrations of CCRP are used to calculate values for the number, affinity, and association of CCRP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide encoding a polypeptide comprising the amino acid sequence selected from the group consisting of SEQ ID NO:1, SEQ ID NO:2, SEQ ID NO:3, SEQ ID NO:4, and SEQ ID NO:5.

2. An isolated and purified polynucleotide which is completely complimentary to the polynucleotide of claim 1.

3. An isolated and purified polynucleotide selected from the group consisting of SEQ ID NO:6, SEQ ID NO:7, SEQ ID NO:8, SEQ ID NO:9, and SEQ ID NO:10.

4. An isolated and purified polynucleotide which is completely complementary to the polynucleotide of claim 3.

5. An expression vector comprising the polynucleotide of claim 1.

6. A host cell containing the expression vector of claim 5.

7. A method for producing a polypeptide comprising the amino acid sequence selected from the group consisting of SEQ ID NO:1, SEQ ID NO:2, SEQ ID NO:3, SEQ ID NO:4, and SEQ ID NO:5, the method comprising the steps of:

(a) culturing the host cell of claim 6 under conditions suitable for the expression of the polypeptide; and (b) recovering the polypeptide from the host cell culture.

\* \* \* \* \*